(12) United States Patent
Johnston (10) Patent No.: US 9,314,475 B2
(45) Date of Patent: Apr. 19, 2016

(54) ORAL AND INJECTABLE FORMULATIONS OF TETRACYCLINE COMPOUNDS

(75) Inventor: Sean Johnston, Doylestown, PA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 571 days.

(21) Appl. No.: 12/414,615

(22) Filed: Mar. 30, 2009

(65) Prior Publication Data

US 2010/0056638 A1  Mar. 4, 2010

Related U.S. Application Data

(60) Provisional application No. 61/040,398, filed on Mar. 28, 2008.

(51) Int. Cl.
*A61K 31/65* (2006.01)
*A61K 9/20* (2006.01)
*A61K 9/00* (2006.01)

(52) U.S. Cl.
CPC ............... *A61K 31/65* (2013.01); *A61K 9/0019* (2013.01); *A61K 9/2054* (2013.01)

(58) Field of Classification Search
CPC .... A61K 31/65; A61K 9/0019; A61K 9/2054
See application file for complete search history.

(56) References Cited

U.S. PATENT DOCUMENTS

| | | | |
|---|---|---|---|
| 2,699,054 A | 1/1955 | Conover | |
| 2,712,517 A | 7/1955 | Gourevitch et al. | |
| 2,886,595 A | 5/1959 | Heinemann et al. | |
| 2,980,584 A | 4/1961 | Hammer | |
| 2,990,331 A | 6/1961 | Neumann et al. | |
| 3,005,023 A | 10/1961 | Miller | |
| 3,019,173 A | 1/1962 | Arishima et al. | |
| 3,019,260 A | 1/1962 | McCormick et al. | |
| 3,062,717 A | 11/1962 | Hammer | |
| 3,165,531 A | 1/1965 | Nelson et al. | |
| 3,200,149 A | 8/1965 | Blackwood et al. | |
| 3,301,899 A | 1/1967 | Kaplan et al. | |
| 3,454,697 A | 7/1969 | Joyner et al. | |
| 3,557,280 A | 1/1971 | Weber et al. | |
| 3,674,859 A | 7/1972 | Beutel et al. | |
| 3,957,980 A | 5/1976 | Noseworthy | |
| 4,018,889 A | 4/1977 | Armstrong | |
| 4,024,272 A | 5/1977 | Rogalski et al. | |
| 4,126,680 A | 11/1978 | Armstrong | |
| 4,837,030 A | 6/1989 | Valorose, Jr. et al. | |
| 5,494,903 A | 2/1996 | Hlavka et al. | |
| 6,465,431 B1 * | 10/2002 | Thorn et al. | 424/1.11 |
| 6,846,939 B2 | 1/2005 | Nelson et al. | |
| 7,326,696 B2 | 2/2008 | Nelson et al. | |
| 7,553,828 B2 | 6/2009 | Nelson et al. | |
| 7,786,099 B2 * | 8/2010 | Nelson | 514/152 |
| 2004/0115261 A1 | 6/2004 | Ashley | |
| 2004/0214801 A1 | 10/2004 | Nelson et al. | |
| 2006/0093677 A1 | 5/2006 | Chickering et al. | |
| 2006/0287283 A1 | 12/2006 | Amoo et al. | |
| 2008/0015169 A1 | 1/2008 | Nelson et al. | |
| 2008/0070873 A1 | 3/2008 | Alekshun et al. | |
| 2009/0246276 A1 * | 10/2009 | Jackson et al. | 424/465 |
| 2009/0325908 A1 | 12/2009 | Nelson et al. | |
| 2010/0113400 A1 | 5/2010 | Nelson et al. | |

FOREIGN PATENT DOCUMENTS

| | | |
|---|---|---|
| EP | 0536515 | 4/1993 |
| GB | 2414668 A * | 7/2005 |
| WO | WO-9911261 A1 | 3/1999 |
| WO | WO-0028983 A1 | 5/2000 |
| WO | WO-0104195 A1 | 1/2001 |
| WO | WO-0204406 A2 | 1/2002 |
| WO | WO-02072532 A1 | 9/2002 |
| WO | WO-03075857 A2 | 9/2003 |
| WO | WO-2004078111 A2 | 9/2004 |
| WO | WO 2004/091513 A2 * | 10/2004 |

OTHER PUBLICATIONS

Kleinebudde 2004, European Journal of Pharmaceutics and Biopharmaceutics, vol. 58, pp. 317-326.*

Chung, J.Y.L. et al., "Synthesis development of an aminomethylcycline antibiotic via an electronically tuned acyliminium Freidel-Crafts reaction" Tetrahedron Letters., vol. 49, pp. 6095-6100 (2008).

Sun et al. "Development of a High Drug Load Tablet Formulation Based on Assessment of Powder Manufacturability: Moving Towards Quality by Design." *Journal of Pharmaceutical Sciences*. vol. 98, No. 1, Jan. 2009:239-247.

"Granulation Manual" (in Japanese), edited by the The Association of Powder Process Industry and Engineering, Japan, published by Ohmsha, Ltd., Feb. 10, 1978, First Edition, Second Issue, pp. 432-444 (partial English translation).

* cited by examiner

*Primary Examiner* — Kara R McMillian
(74) *Attorney, Agent, or Firm* — McCarter & English, LLP; Elizabeth A. Hanley (57) ABSTRACT

Injectable and oral formulations of a tetracycline compound are described. In one embodiment, the invention pertains to an oral formulation of a 9-aminomethyl tetracycline compound, or a salt thereof, in tablet form or capsule. The formulations may be used, for example, to treat infections.

22 Claims, 2 Drawing Sheets

ORAL AND INJECTABLE FORMULATIONS OF TETRACYCLINE COMPOUNDS

RELATED APPLICATION

This application claims the benefit of priority under 35 U.S.C. 119(e) to pending U.S. Provisional Application No. 61/040,398, filed on Mar. 28, 2008, the entire contents of which are incorporated herein by reference.

BACKGROUND

The development of the tetracycline antibiotics was the direct result of a systematic screening of soil specimens collected from many parts of the world for evidence of microorganisms capable of producing bactericidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454, 697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., *pneumococci* and *Salmonella*). The rise of tetracycline resistant organisms has resulted in a general decline in use of tetracyclines and tetracycline analogue compositions as antibiotics of choice.

SUMMARY OF THE INVENTION

In one embodiment, the invention pertains, at least in part, to an oral formulation of a 9-aminomethyl tetracycline compound, e.g., 9-[(2,2-dimethyl-propyl amino)-methyl]-minocycline, or a salt thereof. The formulation may be in the form of a tablet or capsule.

In a further embodiment, the invention also pertains to an oral formulation comprises about 15% to about 30%, about 16% to about 28%, about 18% to about 25%, about 19% to about 22%, about 19.5% to about 21.5%, or about 20% weight percent of the active ingredient, e.g., 9-[(2,2-dimethyl-propyl amino)-methyl]-minocycline or a salt thereof (e.g., tosylate salt).

In yet another embodiment, the invention also pertains to an oral formulation comprises a tablet with a core which weighs about 450 mg to about 550 mg, about 480 mg to about 520 mg, about 490 mg to about 510 mg, about 495 mg to about 505 mg, or about 500 mg.

In a further embodiment, the invention also pertains to an oral formulation comprises about 70 mg to about 200 mg, about 80 mg to about 180 mg, about 90 mg to about 160 mg, about 100 mg to about 140 mg, about 120 mg to 135 mg, or about 132.8 mg equivalent of the active ingredient, e.g., 9-[(2, 2-dimethyl-propyl amino)-methyl]-minocycline, tosylate salt.

In another embodiment, the invention also pertains to a tablet formulation with a mean hardness of about 2 Kp to about 20 Kp, about 3 Kp to about 18 Kp, about 4 Kp to about 16 Kp, about 5 Kp to about 15 Kp, about 6 Kp to about 15 Kp, about 6.3 Kp to about 14.5 Kp, about 6.3 Kp to about 10 Kp, about 6.3 Kp to about 8 Kp, about 6.3 Kp to about 7 Kp, or about 6.3 Kp to about 6.8 Kp. In a further embodiment, the invention also pertains to a tablet formulation with a mean hardness of about 6.5 Kp.

In yet another embodiment, the invention also pertains to a tablet formulation with a disintegration time of about 5 min to about 30 min, about 7 min to about 28 min, about 8 min to about 25 min, about 9 min to about 23 min, about 10 min to about 22 min, or about 11 min to about 21 min. In a further embodiment, the invention also pertains to a tablet formulation with a disintegration time longer than 30 min.

In a further embodiment, the invention also pertains to a tablet which comprises: about 5-40% weight percent of 9-[(2, 2-dimethyl-propyl amino)-methyl]-minocycline or a salt thereof (e.g., tosylate salt); about 50-90% weight percent of a diluent; about 0.01-0.5% weight percent of a stabilizer; about 0.2-2.0% weight percent of a glidant; about 3-10% weight percent of a disintegrant; about 3-10% weight percent of a lubricant; optionally about 0.5-3.0% weight percent of a buffering agent; optionally about 0.1-2.0% weight percent of an antiadherent; and optionally about 1-6% weight percent of a coating component such as a coating colorant. It will be appreciated that, in the context of excipients and other additives, use of the term "a" or "an" (e.g., "a diluent" or "an antiadherent") is also meant to include instances where a plurality of different compounds are used to serve the same function. Thus, for example, a formulation with "a diluent" in the amount of 50-90% includes instances wherein a single compound serves as a diluent and is present in the amount, as well as instances wherein two, three, or more different compounds serve as diluents and together are present in the amount.

In yet another further embodiment, the invention includes tablets which comprise: about 13-30% weight percent of 9-[(2,2-dimethyl-propyl amino)-methyl]-minocycline, tosylate salt; about 10-60% weight percent lactose; about 10-50% weight percent microcrystalline cellulose; about 0.05-0.25% weight percent sodium bisulfite; about 0.4-1.6% weight percent silicon dioxide; about 4.5-6.5% weight percent magnesium stearate or sodium stearyl fumarate; about 4-6% weight percent crospovidone; optionally about 1.0-2.0% weight percent citric acid; optionally about 0.7-1.2% weight percent talc; optionally about 3-5% of Eudragit E100, and about 1-10% weight percent OPADRY® AMB Red. It will be appreciated that, when 9-[(2,2-dimethyl-propyl amino)-methyl]-minocycline is present as a salt, the weight percent range will include the weight of the free base and the salt counterion (unless such weight percentages are reported separately, as exemplified in Table 1).

In yet another further embodiment, the invention also includes tablets which consist of about 13-30% weight percent of 9-[(2,2-dimethyl-propyl amino)-methyl]-minocycline, tosylate salt; about 15-25% weight percent lactose; about 35-45% weight percent microcrystalline cellulose; about 0.17-0.22% weight percent sodium bisulfite; about 0.9-1.1% weight percent silicon dioxide; about 4.5-5.5% weight percent magnesium stearate or sodium stearyl fumarate; about 4.5-5.5% weight percent crospovidone; no citric acid; no talc; no Eudragit E100, and about 3-4.5% OPADRY® AMB Red. In a further embodiment, the tablet of the invention consists essentially of the above listed components.

In yet another further embodiment, the invention also includes tablets which consist of about 15-30% weight percent of 9-[(2,2-dimethyl-propyl amino)-methyl]-minocycline, tosylate salt; about 15-25% weight percent lactose; about 35-45% weight percent microcrystalline cellulose; about 0.17-0.22% weight percent sodium bisulfite; about 0.4-0.6% weight percent silicon dioxide; about 4.5-5.5% weight percent magnesium stearate; about 4.5-5.5% weight percent crospovidone; about 0.9-1.1% talc. In a further embodiment, the tablet of the invention consists essentially of the above listed components.

In yet another further embodiment, the invention also includes tablets which consist of about 26.56% weight percent of 9-[(2,2-dimethyl-propyl amino)-methyl]-minocycline, tosylate salt; about 20.00% weight percent lactose; about 41.74% weight percent microcrystalline cellulose; about 0.20% weight percent sodium bisulfite; about 0.50% weight percent silicon dioxide; about 5.00% weight percent magnesium stearate; about 5.00% weight percent crospovidone; about 1.00% weight percent talc. In a further embodiment, the tablet of the invention consists essentially of the above listed components.

In yet another further embodiment, the invention also includes tablets which consist of about 13-14% weight percent of 9-[(2,2-dimethyl-propyl amino)-methyl]-minocycline, tosylate salt; about 45-55% weight percent lactose; about 15-25% weight percent microcrystalline cellulose; about 0.07-0.12% weight percent sodium bisulfite; about 0.4-0.55% weight percent silicon dioxide; about 5.5-6.0% weight percent magnesium stearate or sodium stearyl fumarate; about 4.5-5% weight percent crospovidone; about 1.25-1.75% weight percent citric acid; about 0.7-1.2% weight percent talc; and about 3-5% of Eudragit E100. In a further embodiment, the tablet of the invention consists essentially of the above listed components.

In yet another further embodiment, the invention also includes a tablet consisting of: about 195-205 mg of 9-[(2,2-dimethyl-propyl amino)-methyl]-minocycline, tosylate salt; about 155-165 mg lactose; about 295-310 mg microcrystalline cellulose; about 1.0-2.0 mg sodium bisulfite; about 30-50 mg crospovidone; about 6-8 mg silicon dioxide; about 30-50 mg magnesium stearate or sodium stearyl fumarate; optionally about 12.5-17.5 mg citric acid; optionally about 7.5-12.5 mg talc; optionally about 30-50 mg of Eudragit E100, and about 20-40 mg of OPADRY® AMB Red.

The invention also pertains, at least in part, to a tablet consisting of: about 202 mg of 9-[(2,2-dimethyl-propyl amino)-methyl]-minocycline, tosylate salt; about 161 mg lactose; about 303 mg microcrystalline cellulose; about 1.5 mg sodium bisulfite; about 37.5 mg crospovidone; about 7.5 mg silicon dioxide; about 37.5 mg sodium stearyl fumarate; and about 30 mg OPADRY® AMB Red.

In yet another further embodiment, the invention also includes a tablet consisting of: about 120-135 mg of 9-[(2,2-dimethyl-propyl amino)-methyl]-minocycline, tosylate salt; about 90-110 mg lactose; about 190-220 mg microcrystalline cellulose; about 0.8-1.2 mg sodium bisulfite; about 20-30 mg crospovidone; about 2-3 mg silicon dioxide; about 20-30 mg magnesium stearate; and about 4-6 mg talc.

The invention also pertains, at least in part, to a tablet consisting of: about 132.80 mg of 9-[(2,2-dimethyl-propyl amino)-methyl]-minocycline, tosylate salt; about 100.00 mg lactose; about 208.70 mg microcrystalline cellulose; about 1.00 mg sodium bisulfite; about 25.00 mg crospovidone; about 2.50 mg silicon dioxide; about 25.00 mg magnesium stearate; and about 5.00 mg talc.

In yet another further embodiment, the invention also includes a tablet consisting of: about 135-140 mg of 9-[(2,2-dimethyl-propyl amino)-methyl]-minocycline, tosylate salt; about 500-525 mg lactose; about 200-210 mg microcrystalline cellulose; about 0.5-1.5 mg sodium bisulfite; about 40-60 mg crospovidone; about 4-5 mg silicon dioxide; about 50-70 mg magnesium stearate; about 12.5-17.5 mg citric acid; about 7.5-12.5 mg talc; and about 30-50 mg of Eudragit E100.

The invention also pertains, at least in part, to a tablet consisting of: about 138.5 mg of 9-[(2,2-dimethyl-propyl amino)-methyl]-minocycline, tosylate salt; about 515 mg lactose; about 205.5 mg microcrystalline cellulose; about 1.0 mg sodium bisulfite; about 50 mg crospovidone; about 5.0 mg silicon dioxide; about 60 mg magnesium stearate; about 15 mg citric acid; about 10 mg talc; and about 40 mg of Eudragit E100.

In another embodiment, the invention also features an oral formulation comprising 90-120 mg of 9-[(2,2-dimethyl-propyl amino)-methyl]-minocycline free base and a pharmaceutically acceptable carrier.

In a further embodiment, the invention features an oral capsule formulation consisting of about 95-115 mg of 9-[(2,2-dimethyl-propyl amino)-methyl]-minocycline free base, 0.95-1.15 mg of sodium bisulfite, about 0.09-0.115 mg of colloidal anhydrous silica, and a capsule.

In yet another embodiment, the invention also pertains, at least in part, to an injectable formulation comprising about 90-110 mg of 9-[(2,2-dimethyl-propyl amino)-methyl]-minocycline free base and a pharmaceutically acceptable carrier (e.g., an aqueous carrier).

The invention also pertains, at least in part, to an injection formulation comprising about 90-110 mg of 9-[(2,2-dimethyl-propyl amino)-methyl]-minocycline free base, a lyoprotectant, an anti-oxidant, and a carrier.

In a further embodiment, the invention pertains, at least in part, to an injectable formulation, comprising about 90-110 mg of 9-[(2,2-dimethyl-propyl amino)-methyl]-minocycline free base, 90-110 mg of sucrose, 0.9-1.1 mg of sodium bisulfite, and an aqueous carrier.

In another further embodiment, the invention also features an injectable formulation, consisting of about 100 mg of 9-[(2,2-dimethyl-propyl amino)-methyl]-minocycline free base, 100 mg of sucrose, 1 mg of sodium bisulfite, pH adjustment compounds and an aqueous carrier.

The invention also features, at least in part, methods for treating subjects using the formulations of the invention. In certain embodiments, the subjects are treated for bacterial infections.

The invention relates to an oral formulation including about 5-40% weight percent of 9-[(2,2-dimethyl-propyl amino)-methyl]-minocycline tosylate salt, about 50-90% weight percent of a diluent, about 0.01-0.5% weight percent of a stabilizer, about 0.2-2.0% weight percent of a glidant, about 1-11% weight percent of a lubricant, about 0.5-10% weight percent of a disintegrant, and optionally 0.5-1.5% of an anti-adherent. For example, the diluent can include lactose, microcrystalline cellulose, or a combination thereof.

In some embodiments, the oral formulation also includes a buffering agent, an antiadherent, a coating component, or a combination thereof.

For example, the oral formulation of the invention includes about 10-30% weight percent of 9-[(2,2-dimethyl-propyl amino)-methyl]-minocycline or a salt thereof; about 50-90% weight percent of a diluent; about 0.01-0.5% weight percent of a stabilizer; about 0.2-2.0% weight percent of a glidant; about 3-10% weight percent of a lubricant; about 3-10% weight percent of a disintegrant, and bout 0.01-0.5% weight percent of an anti-adherent.

One example of the oral formulation includes about 26-28% weight percent of 9-[(2,2-dimethyl-propyl amino)-methyl]-minocycline tosylate salt; about 10-30% weight percent lactose; about 30-50% weight percent microcrystalline cellulose; about 0.05-0.35% weight percent sodium bisulfite; about 0.5-1.5% weight percent silicon dioxide; about 4.5-6.0% weight percent sodium stearyl fumarate or magnesium stearate; about 4-6% weight percent crospovidone; and about 0.5-1.5% weight percent of talc.

On example of an oral formulation includes about 26-28% weight percent of 9-[(2,2-dimethyl-propyl amino)-methyl]-minocycline, tosylate salt; about 15-25% weight percent lactose; about 35-45% weight percent microcrystalline cellulose; about 0.15-0.25% weight percent sodium bisulfite; about 0.8-1.2% weight percent silicon dioxide; about 4.8-5.2% weight percent sodium stearyl fumarate or magnesium stearate; about 4.8-5.2% weight percent crospovidone; about 0.15-0.25% weight percent talc and about 3-5% of OPADRY® AMB Red.

In one embodiment, the oral formulation comprises about 90-250 mg of 9-[(2,2-dimethyl-propyl amino)-methyl]-minocycline or a salt thereof.

For example, the oral formulation is in the form of a tablet containing about 125-140 mg of 9-[(2,2-dimethyl-propyl amino)-methyl]-minocycline, tosylate salt; about 90-110 mg lactose; about 200-220 mg microcrystalline cellulose; about 0.75-1.5 mg sodium bisulfite; about 20-30 mg crospovidone; about 2-3 mg silicon dioxide; about 20-30 mg magnesium stearate; about 4.5-5.5 mg talc and about 20-40 mg of OPADRY® AMB Red.

The invention also relates to an oral formulation of 9-[(2,2-dimethyl-propyl amino)-methyl]-minocycline or a salt thereof present in an amount of more than 10% by weight based on the total weight of the formulation. For example, the formulation is a tablet having a total weight of about 500 mg.

The invention also relates to a compressed solid dosage form comprising 9-[(2,2-dimethyl-propyl amino)-methyl]-minocycline or a salt thereof and at least one pharmaceutically acceptable diluent, wherein the 9-[(2,2-dimethyl-propyl amino)-methyl]-minocycline or a salt thereof is present in an amount that is about 20% by weight based on the total weight of the compressed solid dosage form. For example, the compressed solid dosage form is a tablet having a total weight of about 500 mg.

The invention also relates to a use of a formulation of 9-[(2,2-dimethyl-propyl amino)-methyl]-minocycline or a salt thereof as described herein in the manufacture of a medicament for treating an infection in a subject.

DETAILED DESCRIPTION OF THE INVENTION

The invention pertains, at least in part, to oral and injectable formulations of a 9-aminomethyl tetracycline compound, e.g., 9-[(2,2-dimethyl-propyl amino)-methyl]-minocycline, or a salt thereof. The formulations of the invention have been found to be useful in the treatment of bacterial infections in subjects, such as humans.

The term "9-amino methyl tetracycline compound" includes compounds with a four-ring core structure similar to that of tetracycline and its analogs (e.g., minocycline, sancycline, doxycycline, methacycline, etc.) substituted at the 9-position with an aminomethyl moiety (e.g., —CH$_2$—NR'R", wherein R' and R" are each independently hydrogen, alkyl, alkenyl, alkynyl, cycloalkyl, aryl alkyl, linked to form a ring, etc.). Preferably, the tetracycline compound is 9-[(2,2-dimethyl-propyl amino)-methyl]-minocycline, or a salt thereof. The structure of 9-[(2,2-dimethyl-propyl amino)-methyl]-minocycline is:

In a further embodiment, 9-[(2,2-dimethyl-propyl amino)-methyl]-minocycline is administered orally as the free base or as the tosylate salt or injected as the free base.

In a further embodiment, the formulations described herein are administered to a patient in need of treatment with the formulations. For example, patients in need of treatment include those having, suspected of having, at risk for contracting, or having previously had an infection such as a bacterial infection.

As used herein, the term "patient" (also, "subject") includes any animal in need of treatment with the formulations herein. Examples include farm animals such as cows, sheep, goats, etc., and humans.

The term "treating" or "treatment" refers to the amelioration, eradication, or diminishment of one or more symptoms of a disorder, e.g., a bacterial infection, to be treated. In certain embodiments, the disorder includes the eradication or elimination of a significant portion of bacteria associated with the infection to be treated. In some instances, the composition of the invention is administered prior to infection, i.e., as prophylactic treatment.

In a further embodiment, the infection may be an infection caused by gram-positive pathogens (e.g., *Staphylococcus aureus* (MSSA), *Staphylococcus aureus*(MRSA), *Enterococcus faecalis, Enterococcus faecium, Enterococcus faecium* (VRE), *Streptococcus pneumoniae, Streptococcus pneumoniae* (PRSP), *Streptococcus pyogenes, Streptococcus agalactiae*, etc.), gram-negative pathogens (e.g., *Haemophilus influenzae, Moraxella catarrhalis, Neisseria gonorrhoeae, Escherichia coli, Shigella* spp., *Salmonella* spp., *Klebsiella pneumoniae, Enterobacter aerogenes, Enterobacter cloacae, Serratia marcescens, Acinetobacter baumannii, Stenotrophomonas maltophilia*, etc.), anaerobic pathogens (e.g.,

*Bacteroides fragilis, Clostridium perfringens*, etc.) and/or atypical pathogens (e.g., *Chlamydia pneumoniae, Legionella pneumophila*, etc.).

Oral Tablet Formulation

In one embodiment, the invention pertains, at least in part, to an oral formulation of a 9-aminomethyl tetracycline compound or a salt thereof in tablet form. Advantageously, the 9-aminomethyl tetracycline compound is 9-[(2,2-dimethylpropyl amino)-methyl]-minocycline and the salt is the tosylate salt.

In a further embodiment, the formulation comprises about 5% to about 40%, about 10% to about 30%, about 10% to about 27%, about 12% to about 25%, about 13% to about 25%, about 14% to about 25%, about 15% to about 24%, about 16% to about 24%, about 16% to about 23%, about 16% to about 22%, about 18% to about 22%, about 19% to about 21%, or about 20.0% weight percent of the active ingredient, e.g., 9-[(2,2-dimethyl-propyl amino)-methyl]-minocycline free base.

In a further embodiment, the formulation comprises about 50% to about 90% of a diluent or inert ingredient. Examples of such diluents include, but are not limited to, lactose and microcrystalline cellulose. In a further embodiment, the formulation comprises about 10% to about 60%, about 10% to about 30%, about 11% to about 29%, about 12% to about 28%, about 13% to about 27%, about 14% to about 26%, about 15% to about 25%, about 16% to about 24%, about 17% to about 23%, about 18% to about 22%, about 19% to about 22%, about 20% to about 22%, or preferably, about 21.5% of lactose.

In another further embodiment, the formulation comprises about 10% to about 50%, about 30% to about 50%, about 31% to about 49%, about 32% to about 48%, about 33% to about 47%, about 34% to about 46%, about 35% to about 45%, about 36% to about 44%, about 37% to about 43%, about 38% to about 42%, about 39% to about 41%, about 40% to about 41%, or preferably, about 40.4% weight percent microcrystalline cellulose.

In another further embodiment, the formulation comprises a stabilizer. The stabilizer may also be an anti-oxidant. Examples of stabilizers include sodium bisulfite. In one embodiment, the formulation comprises about 0.01% to about 0.5%, about 0.02% to about 0.45%, about 0.04% to about 0.4%, about 0.05% to about 0.35%, about 0.10% to about 0.3%, about 0.15% to about 0.25%, about 0.16% to about 0.24%, about 0.17% to about 0.23%, about 0.18% to about 0.22%, about 0.19% to about 0.21%, or about 0.2% weight percent sodium bisulfite.

In another further embodiment, the formulation comprises a glidant, such as colloidal silicon dioxide. In one embodiment, the formulation comprises about 0.1% to about 2.0%, about 0.3% to about 1.9%, about 0.5% to about 1.5%, about 0.7% to about 1.4%, about 0.8% to about 1.2%, or about 1.0% weight percent of colloidal silicon dioxide.

In yet another further embodiment, the formulation also comprises a lubricant, such as magnesium stearate or sodium stearyl fumarate. In one embodiment, the formulation comprises about 1% to about 11%, about 2% to about 10%, about 3% to about 9%, about 4% to about 8%, about 4% to about 7%, about 4.5% to about 6%, or about 5.0% weight percent of magnesium stearate or sodium stearyl fumarate.

In yet another further embodiment, the formulation also comprises a disintegrant, such as crospovidone. In one embodiment, the formulation comprises about 0.5% to about 10%, about 1% to about 10%, about 2% to about 9%, about 3% to about 8%, about 4% to about 7%, about 4% to about 6%, or about 5.0% weight percent of crospovidone.

In yet another further embodiment, the tablet formulation also may comprise a buffering agent, such as citric acid. When present, the citric acid may be present in about 0.9% to about 2.0%, about 1.0% to about 1.9%, about 1.1% to about 1.8%, about 1.2% to about 1.7%, about 1.3% to about 1.6%, about 1.4% to about 1.5% or about 1.44% weight percent.

In yet another further embodiment, the tablet formulation also may comprise an anti-adherent, such as talc. When present, the talc may be present in a weight percentage of about 0.1% to about 2.0%, about 0.2% to about 1.9%, about 0.3% to about 1.8%, about 0.4% to about 1.7%, about 0.4% to about 1.6%, about 0.5% to about 1.5%, about 0.6% to about 1.4%, about 0.7% to about 1.3%, about 0.8% to about 1.2%, about 0.9% to about 1.1% or about 0.96% weight percent.

The oral formulation may also comprise a coating. When present, the coating may optionally comprise Eudragit E100 and may optionally comprise trace amount of solvent (preferably less than about 0.1% of ethanol). In one embodiment, the formulation comprises about 1% to about 8%, about 2% to about 7%, about 2% to about 6%, about 2% to about 5%, about 3% to about 4%, or about 3.4% weight percent Eudragit E100.

The oral formulation may also comprise a coating colorant, such as OPADRY® AMB Red. In one embodiment, the formulation comprises about 1% to about 8%, about 2% to about 7%, about 2% to about 6%, about 2% to about 5%, about 3% to about 4%, or about 3.85% weight percent OPADRY® AMB Red.

In another embodiment, the invention pertains to a tablet that comprises about 190 to about 205 mg of a 9-aminomethyl tetracycline compound, e.g., 9-[(2,2-dimethylpropyl amino)-methyl]-minocycline, tosylate salt. Preferably, the tablet comprises about 201.6 mg of 9-[(2,2-dimethyl-propyl amino)-methyl]-minocycline, tosylate salt (i.e., 150 mg of 9-[(2,2-dimethylpropyl amino)-methyl]-minocycline and 51.6 mg of tosylate counterion).

In another further embodiment, the tablet comprises about 140 mg to about 180 mg, about 145 mg to about 175 mg, about 150 mg to about 170 mg, 155 mg to about 165 mg or about 161.1 mg of a diluent, such as lactose.

In another further embodiment, the tablet comprises about 290 mg to about 315 mg, about 295 mg to about 310 mg, about 295 mg to about 305 mg, about 300 mg to about 305 mg, or about 303.3 mg of an additional diluent, e.g., microcrystalline cellulose.

The tablet composition may also further comprise a stabilizer. The stabilizer may be sodium bisulfite, which is also an antioxidant. In one embodiment, the composition comprises about 0.1 mg to about 2 mg, about 0.2 mg to about 2 mg, about 0.3 mg to about 2 mg, about 0.4 mg to about 2 mg, about 0.5 mg to about 1.9 mg, about 0.6 mg to about 1.8 mg, about 0.7 mg to about 1.7 mg, about 0.8 mg to about 1.6 mg, about 0.9 mg to about 1.5 mg, about 1.0 mg to about 1.5 mg, about 1.0 mg to about 2.0, about 1.1 mg to about 1.9 mg, about 1.2 mg to about 1.8 mg, about 1.3 mg to about 1.7 mg, about 1.4 mg to about 1.6 mg, or about 1.5 mg of sodium bisulfite per tablet.

In yet another further embodiment, the tablet comprises about 10 mg to about 100 mg, about 20 mg to about 80 mg, about 30 mg to about 60 mg, about 30 mg to about 50 mg, about 35 mg to about 45 mg, about 35 mg to about 40 mg, or about 37.5 mg of a disintegrant, e.g., crospovidone.

In yet another further embodiment, the tablet comprises a glidant, e.g., colloidal silicon dioxide. The tablet may comprise about 1.0 mg to about 12.0 mg, about 2.0 mg to about 11.0 mg, about 3.0 mg to about 10.0 mg, about 4.0 mg to about 9.0 mg, about 5.0 mg to about 8.0 mg, about 6.0 mg to about 8.0 mg, about 7.0 mg to about 8.0 mg, or about 7.5 mg of a glidant, such as colloidal silicon dioxide.

In yet another further embodiment, the tablet comprises about 10 mg to about 110 mg, about 20 mg to about 90 mg, about 25 mg to about 70 mg, about 30 mg to about 50 mg, about 35 mg to about 40 mg, or about 37.5 mg of a lubricant, e.g., magnesium stearate or sodium stearyl fumarate.

In yet another further embodiment, the tablet may comprise a buffering agent such as citric acid, although other acids may be used. When present, the buffering agent may be present in amount of about 10 mg to about 20 mg, about 11 mg to about 19 mg, about 12 mg to about 18 mg, about 13 mg to about 17 mg, about 14 mg to about 16 mg, or about 15 mg of buffering agent, e.g., citric acid.

The tablet may also comprise an antiadherent to keep to tablets from sticking. In one embodiment, the antiadherent is talc. When present, the composition comprises about 1 mg to about 20 mg, about 2 mg to about 19 mg, about 3 mg to about 18 mg, about 4 mg to about 17 mg, about 5 mg to about 16 mg, about 6 mg to about 15 mg, about 7 mg to about 14 mg, about 8 mg to about 13 mg, about 9 mg to about 12 mg, about 9 mg to about 11 mg or about 10 mg of antiadherent, e.g., talc, per tablet.

In yet another further embodiment, the tablet may comprise a coating component. Examples of coating components include colorants and coating polymers. Specific examples include OPADRY® AMB Red and Eudragit E100.

In yet another further embodiment, the tablet may comprise a coating colorant such as OPADRY® AMB Red, although other colorants may be used. The tablet may comprise about 10 mg to about 50 mg, or about 15 mg to about 45 mg, or about 20 mg to about 40, or about 25 mg to about 35 mg, or about 30 mg of colorant.

The coating may be put on the tablet using a solvent such as ethanol. The composition may comprise trace amounts of ethanol. In a further embodiment, the coating comprises Eudragit E100. The Eudragit E100 may be present in an amount of about 10 mg to about 90 mg, about 20 mg to about 80 mg, about 30 mg to about 70 mg, about 30 mg to about 60 mg, about 30 mg to about 50 mg, or about 40 mg per tablet.

In a further embodiment, the formulation comprises 15% to about 30%, about 16% to about 28%, about 18% to about 25%, about 19% to about 22%, about 19.5% to about 21.5%, or about 20% weight percent of the active ingredient, e.g., 9-[(2,2-dimethyl-propyl amino)-methyl]-minocycline tosylate salt.

In a further embodiment, the formulation comprises about 50% to about 90% of a diluent or inert ingredient. Examples of such diluents include, but are not limited to, lactose and microcrystalline cellulose. In a further embodiment, the formulation comprises about 10% to about 60%, about 10% to about 30%, about 11% to about 29%, about 12% to about 28%, about 13% to about 27%, about 14% to about 26%, about 15% to about 25%, about 16% to about 24%, about 17% to about 23%, about 18% to about 22%, about 19% to about 22%, about 19.5% to about 21.5%, or preferably, about 20% of lactose.

In another further embodiment, the formulation comprises about 30% to about 50%, about 31% to about 50%, about 32% to about 49%, about 33% to about 48%, about 34% to about 47%, about 35% to about 46%, about 36% to about 45%, about 37% to about 44%, about 38% to about 43%, about 39% to about 42%, about 40% to about 42%, or preferably, about 41.74% weight percent microcrystalline cellulose.

In another further embodiment, the formulation comprises a stabilizer. The stabilizer may also be an anti-oxidant. Examples of stabilizers include sodium bisulfite. In one embodiment, the formulation comprises about 0.01% to about 0.5%, about 0.02% to about 0.45%, about 0.04% to about 0.4%, about 0.05% to about 0.35%, about 0.10% to about 0.3%, about 0.15% to about 0.25%, about 0.16% to about 0.24%, about 0.17% to about 0.23%, about 0.18% to about 0.22%, about 0.19% to about 0.21%, or about 0.2% weight percent sodium bisulfite.

In another further embodiment, the formulation comprises a glidant, such as colloidal silicon dioxide. In one embodiment, the formulation comprises about 0.1% to about 1.5%, about 0.2% to about 1.0%, about 0.3% to about 0.8%, about 0.4% to about 0.6%, or about 0.5% weight percent of colloidal silicon dioxide.

In yet another further embodiment, the formulation also comprises a lubricant, such as magnesium stearate. In one embodiment, the formulation comprises about 1% to about 11%, about 2% to about 10%, about 3% to about 9%, about 4% to about 8%, about 4% to about 7%, about 4.5% to about 6%, or about 5.0% weight percent of magnesium stearate.

In yet another further embodiment, the formulation also comprises a disintegrant, such as crospovidone. In one embodiment, the formulation comprises about 0.5% to about 10%, about 1% to about 10%, about 2% to about 9%, about 3% to about 8%, about 4% to about 7%, about 4% to about 6%, or about 5.0% weight percent of crospovidone.

In yet another further embodiment, the tablet formulation also may comprise an anti-adherent, such as talc. When present, the talc may be present in a weight percentage of about 0.1% to about 2.0%, about 0.2% to about 1.9%, about 0.3% to about 1.8%, about 0.4% to about 1.7%, about 0.4% to about 1.6%, about 0.5% to about 1.5%, about 0.6% to about 1.4%, about 0.7% to about 1.3%, about 0.8% to about 1.2%, about 0.9% to about 1.1% or about 1.00% weight percent.

In another embodiment, the invention pertains to a tablet that comprises about 70 mg to about 200 mg, about 80 mg to about 180 mg, about 90 mg to about 160 mg, about 100 mg to about 140 mg, or about 120 mg to 135 mg of a 9-[(2,2-dimethylpropyl amino)-methyl]-minocycline, tosylate salt. Preferably, the tablet comprises about 132.8 mg of 9-[(2,2-dimethyl-propyl amino)-methyl]-minocycline, tosylate salt.

In another further embodiment, the tablet comprises about 50 mg to about 150 mg, about 60 mg to about 140 mg, about 70 mg to about 130 mg, 80 mg to about 120 mg, 90 mg to about 110 mg or about 100 mg of a diluent, such as lactose.

In another further embodiment, the tablet comprises about 150 mg to about 250 mg, about 170 mg to about 230 mg, about 180 mg to about 220 mg, about 190 mg to about 210 mg, or about 208.70 mg of an additional diluent, e.g., microcrystalline cellulose.

The tablet composition may also further comprise a stabilizer. The stabilizer may be sodium bisulfite, which is also an antioxidant. In one embodiment, the composition comprises about 0.1 mg to about 2 mg, about 0.2 mg to about 1.9 mg, about 0.3 mg to about 1.8 mg, about 0.4 mg to about 1.7 mg, about 0.5 mg to about 1.6 mg, about 0.6 mg to about 1.5 mg, about 0.7 mg to about 1.4 mg, about 0.8 mg to about 1.3 mg, about 0.9 mg to about 1.2 mg, about 0.95 mg to about 1.1 mg, or about 1.0 mg of sodium bisulfite per tablet.

In yet another further embodiment, the tablet comprises about 5 mg to about 80 mg, about 10 mg to about 60 mg, about 15 mg to about 40 mg, about 18 mg to about 35 mg, about 20 mg to about 30 mg, about 22 mg to about 28 mg, or about 25.0 mg of a disintegrant, e.g., crospovidone.

In yet another further embodiment, the tablet comprises a glidant, e.g., colloidal silicon dioxide. The tablet may comprise about 0.5 mg to about 10.0 mg, about 0.7 mg to about 8.0 mg, about 1.0 mg to about 6.0 mg, about 1.3 mg to about 4.0 mg, about 1.8 mg to about 3.0 mg, about 2.1 mg to about 2.8 mg, about 2.4 mg to about 2.6 mg, or about 2.5 mg of a glidant, such as colloidal silicon dioxide.

In yet another further embodiment, the tablet comprises about 5 mg to about 80 mg, about 10 mg to about 60 mg, about 15 mg to about 40 mg, about 18 mg to about 35 mg, about 20 mg to about 30 mg, about 22 mg to about 28 mg, or about 25.0 mg of a lubricant, e.g., magnesium stearate.

The tablet may also comprise an antiadherent to keep to tablets from sticking. In one embodiment, the antiadherent is talc. The composition comprises about 1 mg to about 10 mg, about 1.5 mg to about 9 mg, about 2.0 mg to about 8 mg, about 2.5 mg to about 7 mg, about 3.0 mg to about 6 mg, about 3.5 mg to about 5.8 mg, about 4.0 mg to about 5.6 mg, about 4.5 mg to about 5.4 mg, about 4.8 mg to about 5.3 mg, about 4.9 mg to about 5.1 mg or about 5 mg of antiadherent, e.g., talc, per tablet.

It will be appreciated that the diluent, stabilizer, disintegrant, glidant, and lubricant components can also be referred to herein as pharmaceutically acceptable carriers in the formulations described herein. Thus, the formulations may be said to comprise, for example, sodium bisulphate, silicon dioxide, lactose, sodium stearyl fumarate, microcrystalline cellulose, or combinations thereof as a pharmaceutically acceptable carrier.

In a further embodiment, the invention also pertains to a tablet which comprises: about 10-15% weight percent of 9-[(2,2-dimethyl-propyl amino)-methyl]-minocycline or a salt thereof (e.g., tosylate salt); about 50-90% weight percent of a diluent; about 0.01-0.5% weight percent of a stabilizer; about 0.2-1.0% weight percent of a glidant; about 3-10% weight percent of a disintegrant; about 3-10% weight percent of a lubricant; about 0.5-3.0% weight percent of a buffering agent; about 0.1-2.0% weight percent of an antiadherent; and about 1-6% weight percent of a coating component.

In yet another further embodiment, the invention also includes tablets which consist of about 15-30% weight percent of 9-[(2,2-dimethyl-propyl amino)-methyl]-minocycline, tosylate salt; about 15-25% weight percent lactose; about 35-45% weight percent microcrystalline cellulose; about 0.17-0.22% weight percent sodium bisulfite; about 0.4-0.6% weight percent silicon dioxide; about 4.5-5.5% weight percent magnesium stearate; about 4.5-5.5% weight percent crospovidone; about 0.9-1.1% weight percent talc. In a further embodiment, the tablet of the invention consists essentially of the above listed components.

In a further embodiment, the invention also includes tablets which consist of about 26.56% weight percent of 9-[(2,2-dimethyl-propyl amino)-methyl]-minocycline, tosylate salt; about 20.00% weight percent lactose; about 41.74% weight percent microcrystalline cellulose; about 0.20% weight percent sodium bisulfite; about 0.50% weight percent silicon dioxide; about 5.00% weight percent magnesium stearate; about 5.00% weight percent crospovidone; about 1.00% weight percent talc. In a further embodiment, the tablet of the invention consists essentially of the above listed components.

In yet another embodiment, the invention also pertains to an oral formulation comprises a tablet with a core which weighs about 450 mg to about 550 mg, about 480 mg to about 520 mg, about 490 mg to about 510 mg, about 495 mg to about 505 mg, or about 500 mg.

In yet another further embodiment, the invention includes tablets which comprise: about 13-14% weight percent of 9-[(2,2-dimethyl-propyl amino)-methyl]-minocycline, tosylate salt; about 40-60% weight percent lactose; about 10-30% weight percent microcrystalline cellulose; about 0.05-0.15% weight percent sodium bisulfite; about 0.4-0.6% weight percent silicon dioxide; about 5-6.5% weight percent magnesium stearate; about 4-6% weight percent crospovidone; about 1.0-2.0% weight percent citric acid; about 0.7-1.2% weight percent talc; and about 3-5% of Eudragit E100.

In yet another further embodiment, the invention also includes tablets which consist of about 13-14% weight percent of 9-[(2,2-dimethyl-propyl amino)-methyl]-minocycline, tosylate salt; about 45-55% weight percent lactose; about 15-25% weight percent microcrystalline cellulose; about 0.07-0.12% weight percent sodium bisulfite; about 0.4-0.55% weight percent silicon dioxide; about 5.5-6.0% weight percent magnesium stearate; about 4.5-5% weight percent crospovidone; about 1.25-1.75% weight percent citric acid; about 0.7-1.2% weight percent talc; and about 3-5% of Eudragit E100. In a further embodiment, the tablet of the invention consists essentially of the above listed components.

In a further embodiment, the invention also pertains to a tablet which comprises: about 10-30% weight percent of 9-[(2,2-dimethyl-propyl amino)-methyl]-minocycline or a salt thereof (e.g., tosylate salt); about 50-90% weight percent of a diluent; about 0.01-0.5% weight percent of a stabilizer; about 0.2-2.0% weight percent of a glidant; about 3-10% weight percent of a disintegrant; about 3-10% weight percent of a lubricant; about 0-3.0% weight percent of a buffering agent; about 0-2.0% weight percent of an antiadherent; and about 1-6% weight percent of a coating component such as a coating colorant.

In yet another further embodiment, the invention also includes tablets which consist of about 13-30% weight percent of 9-[(2,2-dimethyl-propyl amino)-methyl]-minocycline, tosylate salt; about 15-25% weight percent lactose; about 35-45% weight percent microcrystalline cellulose; about 0.17-0.22% weight percent sodium bisulfite; about 0.9-1.1% weight percent silicon dioxide; about 4.5-5.5% weight percent magnesium stearate or sodium stearyl fumarate; about 4.5-5.5% weight percent crospovidone; no citric acid; no talc; no Eudragit E100, and about 3-4.5% OPADRY® AMB Red. In a further embodiment, the tablet of the invention consists essentially of the above listed components.

In yet another further embodiment, the invention also includes a tablet consisting of: about 195-205 mg of 9-[(2,2-dimethyl-propyl amino)-methyl]-minocycline, tosylate salt; about 155-165 mg lactose; about 295-310 mg microcrystalline cellulose; about 1.0-2.0 mg sodium bisulfite; about 30-50 mg crospovidone; about 6-8 mg silicon dioxide; about 30-50 mg magnesium stearate or sodium stearyl fumarate; optionally about 12.5-17.5 mg citric acid; optionally about 7.5-12.5 mg talc; optionally about 30-50 mg of Eudragit E100, and about 20-40 mg of OPADRY® AMB Red.

In yet another further embodiment, the invention also includes a tablet consisting of: about 135-140 mg of 9-[(2,2-dimethyl-propyl amino)-methyl]-minocycline, tosylate salt; about 500-525 mg lactose; about 200-210 mg microcrystalline cellulose; about 0.5-1.5 mg sodium bisulfite; about 40-60 mg crospovidone; about 4-6 mg silicon dioxide; about 50-70 mg magnesium stearate; about 12.5-17.5 mg citric acid; about 7.5-12.5 mg 15 talc; and about 30-50 mg of Eudragit E100.

The invention also pertains, at least in part, to a tablet consisting of: about 138.5 mg of 9-[(2,2-dimethyl-propyl amino)-methyl]-minocycline, tosylate salt; about 515 mg lactose; about 205.5 mg microcrystalline cellulose; about 1.0 mg sodium bisulfite; about 50 mg crospovidone; about 5.0 mg silicon dioxide; about 60 mg magnesium 20 stearate; about 15 mg citric acid; about 10 mg talc; and about 40 mg of Eudragit E100.

The tablets of the invention can be formed using direct compression methods. For example, the tablets can be formed using a pressure of about 20 kPa and can be made into coated tablets such as oval shaped tablets.

The tablets of the invention can be formed using a roller compaction method. For example, the tablets formed by a roller compaction method can have hardness of 2 Kp to about 20 Kp, about 3 Kp to about 18 Kp, about 4 Kp to about 16 Kp, about 5 Kp to about 15 Kp, about 6 Kp to about 15 Kp, about 6.3 Kp to about 14.5 Kp, about 6.3 Kp to about 10 Kp, about 6.3 Kp to about 8 Kp, about 6.3 Kp to about 7 Kp, or about 6.3 Kp to about 6.8 Kp. For example, the tablets have a mean hardness of about 6.5 Kp.

In one embodiment, the formulation process uses roller compaction to increase the particle size of the blend. For example, in some embodiments, roller compaction allows higher drug loading in the formulation, such as drug loading of greater than 10% weight percent.

In one embodiment, the tablets are formulated according to the amounts in Table 1 below.

TABLE 1

| Material | mg/tablet | % w/w | Function |
|---|---|---|---|
| 9-[(2,2-dimethyl-propyl amino)-methyl]-minocycline | 150 (active) | 20.0 (active) | Active |
| Tosylate and other API impurities[1] | 51.6 | 6.9 | API counter ion |
| Lactose[2] | 161.1 | 21.5 | Diluent |
| Microcrystalline cellulose | 303.3 | 40.4 | Diluent |
| Sodium bisulfite | 1.5 | 0.2 | Stabilizer |
| Crospovidone | 37.5 | 5.0 | Disintegrant |
| Colloidal silicon dioxide | 7.5 | 1.0 | Glidant |
| Sodium stearyl fumarate | 37.5 | 5.0 | Lubricant |
| Total Coated tablet | 750.0 | 100.0 | |
| OPADRY ® AMB Red | ~30.0 | 3.85 | Color coating |
| Total | 780.00 | | |

In another embodiment, the tablets are formulated according to the amounts in Table 2 below

TABLE 2

| Material | mg/Tablet | % w/w |
|---|---|---|
| 9-[(2,2-dimethyl-propyl amino)-methyl]-minocycline tosylate | 132.80 | 26.56 |
| Lactose | 100.00 | 20.00 |
| Microcrystalline cellulose 200 | 208.70 | 41.74 |
| Sodium bisulfite | 1.00 | 0.20 |
| Silicone dioxide | 2.50 | 0.50 |
| Crospovidone | 25.00 | 5.00 |
| Talc | 5.00 | 1.00 |
| Magnesium stearate | 25.00 | 5.00 |
| Total | 500.0 | 100.0 |

Oral Capsule Formulations

In another embodiment, the invention also features an oral formulation comprising about 90-120 mg of a 9-aminomethyl tetracycline compound, e.g., 9-[(2,2-dimethyl-propyl amino)-methyl]-minocycline or a salt thereof and a pharmaceutically acceptable carrier. In a further embodiment, the 9-[(2,2-dimethyl-propyl amino)-methyl]-minocycline is a free base.

In another embodiment, the invention also features an oral formulation comprising about 70-200 mg of a 9-[(2,2-dimethyl-propyl amino)-methyl]-minocycline, tosylate salt.

In another further embodiment, the pharmaceutically acceptable carrier comprises a stabilizer and/or anti-oxidant such as sodium bisulfite. The composition may also comprise a glidant, such as silica, e.g., colloidal anhydrous silica.

The formulation may be placed in a capsule such as, for example, a white HPMC opaque capsule, size 0.

In a further embodiment, the oral capsule formulation comprises about 95 mg to about 115 mg, about 100 mg to about 110 mg, or about 105 mg of 9-[(2,2-dimethylpropyl amino)-methyl]-minocycline free base.

The formulation may also comprise about 0.95 to about 1.15 mg, about 0.10 mg to about 1.10 mg, or about 1.05 mg of sodium bisulfite, and about 0.09 mg to about 0.115 mg, about 0.10 mg to about 0.11 mg, or about 0.105 mg of colloidal anhydrous silica. It will be appreciated that colloidal anhydrous silica can also be referred to as a pharmaceutically acceptable carrier in the formulations described herein.

In a further embodiment, the invention features an oral capsule formulation consisting of about 95-115 mg of 9-[(2, 2-dimethyl-propyl amino)-methyl]-minocycline free base, 0.95-1.15 mg of sodium bisulfite, about 0.09-0.115 mg of colloidal anhydrous silica, and a capsule.

In another embodiment, the oral capsule formulation comprises about 70 mg to about 200 mg, about 80 mg to about 180 mg, about 90 mg to about 160 mg, about 100 mg to about 140 mg, or about 120 mg to 135 mg of a 9-[(2,2-dimethyl-propyl amino)-methyl]-minocycline, tosylate salt. Preferably, the capsule comprises about 132.8 mg of 9-[(2,2-dimethyl-propyl amino)-methyl]-minocycline, tosylate salt.

In a further embodiment, the capsule formulation may also comprise about 120-135 mg of 9-[(2,2-dimethyl-propyl amino)-methyl]-minocycline, tosylate salt; about 90-110 mg lactose; about 190-220 mg microcrystalline cellulose; about 0.8-1.2 mg sodium bisulfite; about 20-30 mg crospovidone; about 2-3 mg silicon dioxide; about 20-30 mg magnesium stearate; and about 4-6 mg talc.

In a further embodiment, the capsule formulation comprises about 132.80 mg of 9-[(2,2-dimethyl-propyl amino)-methyl]-minocycline, tosylate salt; about 100.00 mg lactose; about 208.70 mg microcrystalline cellulose; about 1.00 mg sodium bisulfite; about 25.00 mg crospovidone; about 2.50 mg silicon dioxide; about 25.00 mg magnesium stearate; and about 5.00 mg talc. In a further embodiment, the tablet of the invention consists essentially of the above listed components.

The capsules may be manufactured using the following process. First, each of the ingredients listed in Table 3 below were prepared individually. The tetracycline compound, 9-[(2,2-dimethyl-propyl amino)-methyl]-minocycline, free base, was passed through a 500 micron screen and weighed in the formulation quantity. Sodium bisulfite was placed into a mortar and milled to break down crystals. Then, the sodium bisulfite was passed through a 300 micron screen and weighed in its formulation quantity. The colloidal anhydrous silica (AEROSIL) was passed through a 710 micron screen and also weighed in its formulation quantity, as shown in Table 3.

TABLE 3

| Material | Quantity[a] |
|---|---|
| 9-[(2,2-dimethyl-propyl amino)-methyl]-minocycline freebasae | 421 g[b] |
| Sodium bisulfite | 4.21 g |
| Colloidal anhydrous silica | 0.425 g |
| White HPMC Opaque capsule size 0 | 4000 |

[a]Minor variations in the quantities (± 10%) may occur during the drug development process.
[b]Corrected quantity After 9-[(2,2-dimethyl-propyl amino)-methyl]-minocycline, free base and sodium bisulfite were both passed through the respective screens, the free base was placed in a stainless steel container and the sodium bisulfite was added. The mixture was blended for ten minutes before the colloidal anhydrous silica (AEROSIL) was added. After the silica was added, the mixture was blended for five minutes. The HPMC capsules were then hand filled and the weights of each are recorded.

Injectable Formulation

In another embodiment, the invention also features an injectable formulation comprising about 90-110 mg of 9-[(2,2-dimethyl-propyl amino)-methyl]-minocycline free base and a pharmaceutically acceptable carrier (e.g., an aqueous carrier).

In a further embodiment, the injection formulation may comprise about 90-110 mg of 9-[(2,2-dimethyl-propyl amino)-methyl]-minocycline and one or more components selected from a free base, a lyoprotectant, an anti-oxidant, a pH adjustment compound, and a carrier.

Examples of lyoprotectant include, for example, sugars such as sucrose. The formulation (e.g., for a vial containing about 100 mg of the tetracycline compound) may comprise about 90 to about 110 mg, about 95 mg to about 105 mg, or about 100 mg of sucrose.

Examples of antioxidants include, but are not limited, to sodium bisulfite. The injectable formulation (e.g., for a vial containing about 100 mg of the tetracycline compound) may comprise about 0.9 to about 1.1 mg, about 0.95 to about 1.05 mg, or about 1.0 mg of sodium bisulfite.

The formulation may also comprise acids and bases which can be used to adjust the pH of the composition to 4.2. Examples of such compounds include hydrochloric acid and sodium hydroxide.

In a further embodiment, the invention pertains, at least in part, to an injectable formulation, comprising about 90-110 mg of 9-[(2,2-dimethyl-propyl amino)-methyl]-minocycline free base, 90-110 mg of sucrose, 0.9-1.1 mg of sodium bisulfite, and an aqueous carrier.

In another further embodiment, the invention also features an injectable formulation, consisting of about 100 mg of 9-[(2,2-dimethyl-propyl amino)-methyl]-minocycline free base, 100 mg of sucrose, 1 mg of sodium bisulfite, pH adjustment compounds and an aqueous carrier.

In Table 4 below, the composition of a batch injectable formulation of 9-[(2,2,dimethyl-propyl amino)-methyl]-minocycline free base for a 100 mg vial is described.

TABLE 4

| Material | Quantity | Function |
| --- | --- | --- |
| 9-[(2,2-dimethyl-propyl amino)-methyl]-minocycline free base | 174.8 g | Active Ingredient |
| Sucrose | 174.8 g | Lyoprotectant |
| Sodium bisulfite | 1.75 g | Anti-oxidant |
| 1M Hydrochloric acid | 402.0 g | pH adjustment |
| 0.1M Hydrochloric acid | As needed to pH 4.2 | pH adjustment |
| 0.1M sodium hydroxide | As needed to pH 4.2 | pH adjustment |
| Water | To a total batch mass of 5.82 Kg | Dissolution medium for sterile filtration |

The injectable formulation may be made by first charging a vessel with water (4.662 liters) and 174.8 grams of sucrose. 372 grams of 1 M hydrochloric acid and 1.75 g of sodium bisulfite were also added. 174.8 g of 9-[(2,2-dimethyl-propyl amino)-methyl]-minocycline free base was then added. After the tetracycline compound was added, the pH was adjusted to 4.0 to 4.5 using 0.1 M sodium hydroxide or 0.1 M hydrochloric acid, as appropriate. The weight of the resulting solution was adjusted to 5.82 kg with additional water. The mixture was then filtered through a sterile 0.22 pm filter. Type 1 glass vials were then filled with 3.5 g of the solution per vial.

An injectable formulation using the tosylate salt of 9-[(2,2-dimethyl-propyl amino)-methyl]-minocycline may also be prepared. Table 5 provides an example formulation.

TABLE 5

| Material | Quantity | Function |
| --- | --- | --- |
| 9-[(2,2-dimethyl-propyl amino)-methyl]-minocycline free base | 591.7 g | Active ingredient |
| Tosylate[1] | 185.5 g | API counter ion |
| Sucrose | 591.7 g | Lyoprotectant |
| Sodium bisulfite | 5.9 g | Anti-oxidant |
| 1M hydrochloric acid | 197.0 g | pH adjustment |
| 2M hydrochloric acid | 150.0 g | pH adjustment |
| 2M sodium hydroxide | 0 g | pH adjustment |
| Water | As needed for a total batch mass of 19.72 Kg | Dissolution medium for sterile filtration |

Roller Compaction

In another embodiment, the invention features an oral tablet formulation consists of: about 120-135 mg of 9-[(2,2-dimethyl-propyl amino)-methyl]-minocycline, tosylate salt; about 90-110 mg lactose; about 190-220 mg microcrystalline cellulose; about 0.8-1.2 mg sodium bisulfite; about 20-30 mg crospovidone; about 2-3 mg silicon dioxide; about 20-30 mg magnesium stearate; and about 4-6 mg talc.

In a further embodiment, the invention features an oral tablet formulation consists of tablets which weigh about 450 mg to about 550 mg, about 480 mg to about 520 mg, about 490 mg to about 510 mg, about 495 mg to about 505 mg, or about 500 mg.

In a further embodiment, the invention features an oral tablet formulation consists of tablets with a mean hardness of about 2 Kp to about 20 Kp, about 3 Kp to about 18 Kp, about 4 Kp to about 16 Kp, about 5 Kp to about 15 Kp, about 6 Kp to about 15 Kp, about 6.3 Kp to about 14.5 Kp, about 6.3 Kp to about 10 Kp, about 6.3 Kp to about 8 Kp, about 6.3 Kp to about 7 Kp, or about 6.3 Kp to about 6.8 Kp. In a preferred embodiment, the invention also features a tablet formulation with a mean hardness of about 6.5 Kp.

In a further embodiment, the invention features an oral tablet formulation consists of tablets prepared by a roller compaction process.

The roller compaction process is illustrated in Scheme 1 below.

The roller compaction process significantly improved the drug load. Due to the physical properties of the 9-[(2,2-dimethyl-propyl amino)-methyl]-minocycline, or a salt thereof (API), e.g. small particle size, poor flow characteristics, tendency to adhere to the faces of the tablet die, and thus the large volume of filler and lubricant needed, a direct compression process achieved 10% drug load, e.g., 100 mg in a in a 1 g tablet. Roller compaction process overcame these limitations and gave a blend with a larger particle size and better flow characteristics, and increased the drug load to 20%.

Step 1: Tablet Formulation

Target tablet core weight is 500 mg. Dose is 100 mg freebase equivalent of active agent, API assay is 75.3%. Formulation data are provided in Table 2.

Step 2: Blending and Granulation

The blend was manufactured and sampled prior to lubrication to determine uniformity. Five samples were removed from throughout the blend. Pre-lubrication data are provided in Table 6.

TABLE 6

| Sample No. | Assay |
|---|---|
| 1 | 20.5% |
| 2 | 21.4% |
| 3 | 20.4% |
| 4 | 20.4% |
| 5 | 21.0% |
| Mean | 20.7% |
| RSD | 2.1% |
| Target | 21.05 |

Uniform blend was achieved. The blend was then lubricated using 5% magnesium stearate and granulated using an Alexanderwerk WP120 Roller compactor, with the following setting:

| Screw feeder speed: | 35 RPM | Rollers: | 25 mm parts |
| Roller speed: | 10 RPM | Pre screen: | 2 mm |
| Pre-granulator: | 65.9 RPM | Fine screen: | 1 mm |
| Fine granulator: | 85 RPM | | |
| Pressure: | 30 Bar | | |
| Gap control: | ON | | |
| Gap set: | 1 mm | | |
| Vacuum: | ON | | |

The granules were sampled to determine uniformity following the lubrication and granulation process. Five samples were removed from throughout the blend. Table 7 provides post-lubrication and granulation sampling data. Uniform granules were obtained.

TABLE 7

| Sample No. | Assay |
|---|---|
| 1 | 20.5% |
| 2 | 20.3% |
| 3 | 20.1% |
| 4 | 20.5% |
| 5 | 20.5% |
| Mean | 20.4% |
| RSD | 0.9% |
| Target | 20.0 |

Figure 1:
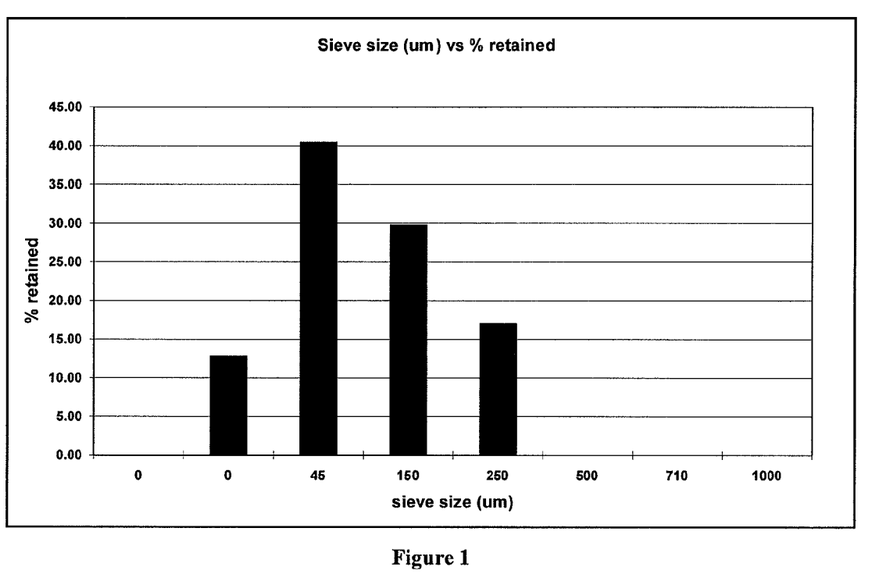
FIG. 1 shows the percentage of particles retained by sieves of different sizes before granulation.
Figure 2:
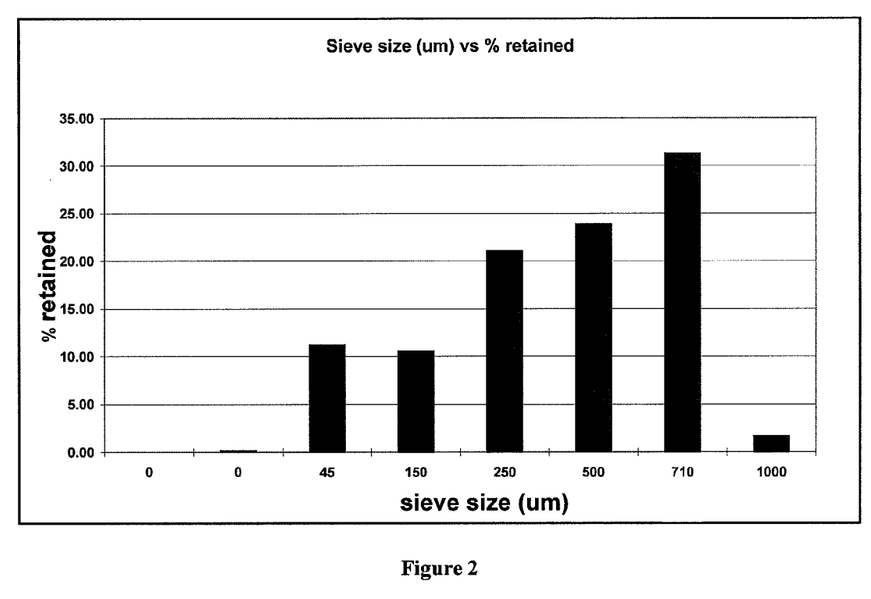
FIG. 2 shows the percentage of particles retained by sieves of different sizes after granulation.

Particle sizing was assessed pre and post granulation. FIGS. 1 and 2 show the percentage retained on the mesh size. The granulation process significantly decreased the fine content. This change in particle improved flow characteristics and decreased the tendency to adhere of the API and thus allowed drug load to be increased.

Step 3: Compression

The granules were used to compress tablets using a Riva Piccola tablet press. The granules flowed well from the hopper. Round normal concave tooling with a 10 mm diameter was used. The tablet weight of 500 mg was achieved. Tablets were compressed to obtain the hardest tablet without stressing the equipment. A range of softer tablets was then compressed. Disintegration was performed on the tablets obtained. Both the tablets weights and hardness values display low variability. Granules flowed well during the compression. Table 8 provides the properties of the tablets.

TABLE 8

| Mean Hardness (Kp) | 6.56 (0.35) | 9.54 (0.25) | 12.63 (0.11) | 14.26 (0.37) |
|---|---|---|---|---|
| Thickness (mm) | 6.32 | 6.10 | 5.93 | 5.87 |
| Tablet weight (mg) | 493.9 (0.35) | 495.8 (2.4) | 492.5 (1.6) | 496.5 (3.0) |
| Disintegration (min) | 11-12 | 18-21 | >30 | >30 |

The remainder of the granules were compressed to a hardness of approximately 6.5 Kp (actual hardness 6.66 Kp SD 0.52). Average tablet weight was 494.0 mg with a RSD of 0.51%.

Step 4: Coating

The tablet batch was divided into two sub lots. One lot was coated with Eudragit E100 using an ethanol-based solution. A 4% weight gain was achieved in 2 hours.

The second lot of tablets was coated by using an aqueous based Opadry® AMB moisture barrier system. The required 4% weight gain was achieved in less that an hour. The tablets produced had little to no visible edge erosion.

It is to be understood that wherever values and ranges are provided herein, e.g., in amounts, dosages, etc., all values and ranges encompassed by these values and ranges, are meant to be encompassed within the scope of the present invention. Moreover, all values in these values and ranges may also be the upper or lower limits of a range.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, issued patents, and published patent applications cited throughout this application are hereby incorporated by reference.

The invention claimed is:

1. An oral formulation in tablet form, comprising about 19% to about 22% weight percent of 9-[(2,2-dimethyl-propyl amino)-methyl]-minocycline or a salt thereof, a diluent, a stabilizer, a glidant, a lubricant, and a disintegrant, wherein the oral formulation is compressed using roller compaction.

2. The oral formulation of claim 1, comprising 90-250 mg of 9-[(2,2-dimethyl-propyl amino)-methyl]-minocycline or a salt thereof.

3. The oral formulation of claim 1, wherein the oral formulation comprises about 20% weight percent of 9-[(2,2-dimethyl-propyl amino)-methyl]-minocycline.

4. The oral formulation of claim 1, wherein the oral formulation comprises about 50% to about 90% weight percent of a diluent.

5. The oral formulation of claim 4, wherein the diluent comprises lactose and microcrystalline cellulose.

6. The oral formulation of claim 5, wherein the oral formulation comprises about 10% to about 30% weight percent of lactose.

7. The oral formulation of claim 5, wherein the oral formulation comprises about 30% to about 50% weight percent of microcrystalline cellulose.

8. The oral formulation of claim 1, wherein the stabilizer is sodium bisulfite.

9. The oral formulation of claim 8, wherein the oral formulation comprises about 0.001% to about 0.5% weight percent of sodium bisulfite.

10. The oral formulation of claim 1, wherein the glidant is colloidal silicon dioxide.

11. The oral formulation of claim 10, wherein the oral formulation comprises about 0.1% to about 1.5% weight percent of colloidal silicon dioxide.

12. The oral formulation of claim 1, wherein the lubricant is sodium stearyl fumarate.

13. The oral formulation of claim 12, wherein the oral formulation comprises about 2% to about 10% weight percent of sodium stearyl fumarate.

14. The oral formulation of claim 1, wherein the disintegrant is crospovidone.

15. The oral formulation of claim 2, wherein the oral formulation comprises:
    about 140 mg to about 180 mg of lactose;
    about 290 mg to about 315 mg of microcrystalline cellulose;
    about 0.1 mg to about 2 mg of sodium bisulfite;
    about 1.0 mg to about 12 mg of silicon dioxide; and
    about 10 mg to about 110 mg of sodium stearyl fumarate.

16. The oral formulation of claim 1, wherein the oral formulation comprises:
    about 50-90% weight percent of a diluent;
    about 0.01-0.5% weight percent of a stabilizer;
    about 0.2-2.0% weight percent of a glidant;
    about 3-10% weight percent of a lubricant;
    about 0-2.0% weight percent of an antiadherent; and
    about 1-6% weight percent of a coating component.

17. The oral formulation of claim 1, wherein the oral formulation comprises:
    about 10 to about 30% weight percent of lactose;
    about 30% to about 50% weight percent of microcrystalline cellulose;
    about 0.001% to about 0.5% weight percent of sodium bisulfite;
    about 0.1% to about 1.5% weight percent of colloidal silicon dioxide; and
    about 2% to about 10% weight percent of sodium stearyl fumarate.

18. The oral formulation of claim 2, wherein the oral formulation comprises:
    about 50 mg to about 150 mg of lactose;
    about 0.5 mg to about 10.0 mg of colloidal silicon dioxide; and
    about 5 mg to about 80 mg of sodium stearyl fumarate.

19. An oral formulation in tablet form, comprising about 19% to about 22% weight percent of 9-[(2,2-dimethyl-propyl amino)-methyl]-minocycline tosylate salt, lactose, microcrystalline cellulose, sodium bisulfite, colloidal silicon dioxide, sodium stearyl fumarate and crosspovidone, wherein the oral formulation is compressed using roller compaction.

20. The oral formulation of claim 19, comprising 90-250 mg of 9-[(2,2-dimethyl-propyl amino)-methyl]-minocycline tosylate salt, lactose, microcrystalline cellulose, sodium bisulfite, colloidal silicon dioxide, sodium stearyl fumarate and crosspovidone.

21. The oral formulation of claim 1, wherein the 9-[(2,2-dimethyl-propyl amino)-methyl]-minocycline or a salt thereof is 9-[(2,2-dimethyl-propyl amino)-methyl]-minocycline tosylate salt.

22. The oral formulation of claim 19, wherein the oral formulation comprises about 20% weight percent of 9-[(2,2-dimethyl-propyl amino)-methyl]-minocycline.

* * * * *